United States Patent
Felton et al.

(10) Patent No.: US 10,874,517 B2
(45) Date of Patent: Dec. 29, 2020

(54) INFLATABLE PENILE PROSTHESIS WITH REINFORCED MEMBERS

(71) Applicant: Boston Scientific Scimed, Inc., Maple Grove, MN (US)

(72) Inventors: Jessica Elizabeth Felton, Minneapolis, MN (US); James Ryan Mujwid, Hudson, WI (US); Scott L. Sjoquist, Orono, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 191 days.

(21) Appl. No.: 15/970,389

(22) Filed: May 3, 2018

(65) Prior Publication Data

US 2018/0318086 A1 Nov. 8, 2018

Related U.S. Application Data

(60) Provisional application No. 62/502,017, filed on May 5, 2017.

(51) Int. Cl.
*A61F 2/26* (2006.01)
*A61F 2/00* (2006.01)

(52) U.S. Cl.
CPC .............. *A61F 2/26* (2013.01); *A61F 2/004* (2013.01); *A61F 2210/0014* (2013.01); *A61F 2230/0069* (2013.01); *A61F 2250/0003* (2013.01); *A61F 2250/0025* (2013.01); *A61F 2250/0026* (2013.01); *A61F 2250/0036* (2013.01)

(58) Field of Classification Search
CPC .............. A61F 2/26; A61F 2/004; A61F 5/41
USPC ..................................... 600/38–41
See application file for complete search history.

(56) References Cited

U.S. PATENT DOCUMENTS

| | | | |
|---|---|---|---|
| 2009/0124851 A1 | 5/2009 | Kuyava et al. |
| 2016/0089241 A1 | 3/2016 | Taylor |
| 2016/0100945 A1 | 4/2016 | Little et al. |

FOREIGN PATENT DOCUMENTS

| | | |
|---|---|---|
| WO | 2013096615 A1 | 6/2013 |
| WO | 2014052729 A2 | 4/2014 |

OTHER PUBLICATIONS

International Search Report and Written Opinion for Application No. PCT/US2018/031010, dated Jul. 10, 2018, 15 pages.

*Primary Examiner* — John P Lacyk
(74) *Attorney, Agent, or Firm* — Brake Hughes Bellermann LLP

(57) ABSTRACT

According to an aspect, an inflatable penile prosthesis includes an inflatable member, the inflatable member having a reinforced portion; a reservoir configured to hold fluid; and a pump assembly configured to facilitate a transfer of the fluid from the reservoir to the inflatable member when the prosthesis is in an inflation mode, and facilitate a transfer of the fluid from the inflatable member to the reservoir when the prosthesis is in a deflation mode.

12 Claims, 8 Drawing Sheets

INFLATABLE PENILE PROSTHESIS WITH REINFORCED MEMBERS

CROSS-REFERENCE TO RELATED APPLICATION

This application is a Nonprovisional of, and claims priority to, U.S. Provisional Patent Application No. 62/502,017, filed on May 5, 2017, entitled "INFLATABLE PENILE PROSTHESIS WITH REINFORCED MEMBERS", which is incorporated by reference herein in its entirety.

TECHNICAL FIELD

This disclosure relates generally to bodily implants and more specifically to inflatable penile prostheses with reinforced members.

BACKGROUND

One treatment for male erectile dysfunction is the implantation of a penile prosthesis that mechanically erects the penis. Some existing penile prostheses include inflatable cylinders or members that can be susceptible to undesired expansion properties. For example, some known inflatable members are formed with fabric or knit materials which can have imperfections. Such imperfections can lead to irregular diametric and length expansion properties. Additionally, some known inflatable members may not provide sufficient stiffness and rigidity when inflated.

Accordingly, it would be useful to provide a bodily implant, such as a penile prosthesis that includes an improved inflatable member.

SUMMARY

According to an aspect, an inflatable penile prosthesis includes an inflatable member, the inflatable member having a reinforced portion; a reservoir configured to hold fluid; and a pump assembly configured to facilitate a transfer of the fluid from the reservoir to the inflatable member when the prosthesis is in an inflation mode, and facilitate a transfer of the fluid from the inflatable member to the reservoir when the prosthesis is in a deflation mode.

In some embodiments, the inflatable member defines a cavity. In some embodiments, the inflatable member includes a sidewall that defines a cavity. In some embodiments, the inflatable member includes a sidewall that defines a cavity, the sidewall having a first portion and a second portion, the first portion of the sidewall having a first thickness, the second portion of the sidewall having a second thickness, the first thickness being greater than the second thickness.

In some embodiments, the inflatable member is configured to stretch. In some embodiments, the inflatable member is formed of a elastomeric polymer.

In some embodiments, the inflatable member includes a sidewall having an outer surface, the outer surface of the including a plurality of projections. In some embodiments, the inflatable member includes a sidewall having an outer surface and an inner surface opposite the outer surface, the inner surface including a plurality of projections. In some embodiments, the inflatable member includes a sidewall having an outer surface and an inner surface opposite the outer surface, the inner surface defining a cavity configured to receive the fluid, the inner surface including a plurality of projections. In some embodiments, the inflatable member includes a sidewall having an outer surface and an inner surface opposite the outer surface, the inner surface being smooth, the outer surface including a plurality of projections. In some embodiments, the inflatable member includes a sidewall having an outer surface and an inner surface opposite the outer surface, the outer surface being smooth, the inner surface including a plurality of projections. In some embodiments, the inflatable member includes a sidewall having an outer surface and an inner surface opposite the outer surface, the outer surface including a plurality of projections, the inner surface including a plurality of projections.

In some embodiments, the inflatable member is formed of a homogenous material.

In some embodiments, the inflatable member includes a frame portion and a casing portion. In some embodiments, the inflatable member includes a frame portion and a casing portion, the casing portion surrounding the frame portion. In some embodiments, the inflatable member includes a frame portion and a casing portion, the frame portion includes a plurality of woven filaments.

According to another aspect, a bodily implant includes an inflatable member, the inflatable member having a sidewall defining a cavity configured to receive fluid, the sidewall including a first portion having a first thickness and a second portion having a second thickness, the first thickness being greater than the second thickness; a reservoir configured to the fluid; and a pump assembly configured to facilitate a transfer of the fluid from the reservoir to the inflatable member.

In some embodiments, the inflatable member is formed of a homogenous material.

According to another aspect, a bodily implant includes an inflatable member, the inflatable member having a frame and a casing; a reservoir configured to the fluid; and a pump assembly configured to facilitate a transfer of the fluid from the reservoir to the inflatable member.

In some embodiments, the casing of the inflatable member surrounds the frame of the inflatable member.

DETAILED DESCRIPTION

Figure 1:
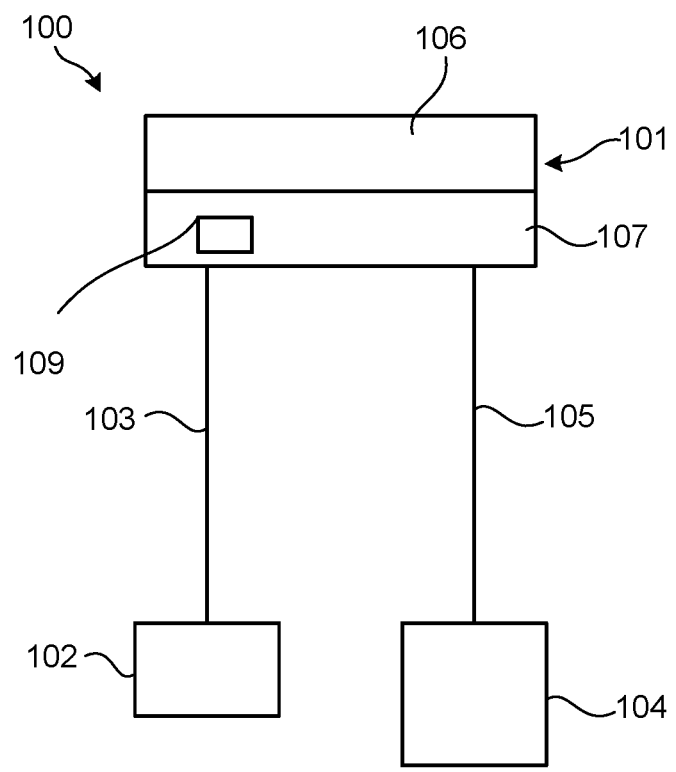
FIG. 1 schematically illustrates an inflatable penile prosthesis according to an embodiment.

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to medical devices such as penile prostheses or other bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure. For example, in some embodiments, the patient may be a human male, a human female, or any other mammal.

The terms proximal and distal described in relation to various devices, apparatuses, and components as discussed in the subsequent text of the present disclosure are referred with a point of reference. The point of reference, as used in this description, is a perspective of a person who implants the inflatable penile prosthesis. The person may be a surgeon, a physician, a nurse, a doctor, a technician, and the like who may perform the implantation procedure. The term proximal refers to an area or portion that is closer or closest to the person during the implantation procedure. The term distal refers to an area or portion that is farther or farthest from the person.

The embodiments discussed herein may improve the performance of an inflatable member of the device. For example, the inflatable member may have improved stiffness or rigidity, improved reliability, improved visualization with imaging devices, such as a MRI or an X-ray device, or improved deflation or inflation times.

The embodiments may include an inflatable penile prosthesis having a pump assembly, an inflatable member, and a reservoir. The inflatable member may be implanted into the corpus cavernosae of a patient or user, the reservoir may be implanted in the user's abdomen, and the pump assembly may be implanted in the scrotum. The pump assembly may switch between an inflation position and a deflation position such that a user can operate the device to place the inflatable penile prosthesis in either an inflation mode to transfer fluid from the reservoir to the inflatable member or a deflation mode to transfer the fluid from the inflatable member back to the reservoir.

FIG. 1 schematically illustrates an inflatable penile prosthesis 100 according to an aspect. The inflatable penile prosthesis 100 may include a reservoir 102, an inflatable member 104, and a pump assembly 101 configured to transfer fluid between the reservoir 102 and the inflatable member 104. In some examples, the inflatable member 104 may be implanted into the corpus cavernosae of the user, the reservoir 102 may be implanted in the abdomen or pelvic cavity of the user (e.g., the reservoir 102 may be implanted in the lower portion of the user's abdominal cavity or the upper portion of the user's pelvic cavity), and the pump assembly 101 may be implanted in the scrotum of the user.

The inflatable member 104 may be capable of expanding upon the injection of fluid into a cavity of the inflatable member 104. For instance, upon injection of the fluid into the inflatable member 104, the inflatable member 104 may increase its length and/or width, as well as increase its rigidity. In some examples, the inflatable member 104 may include a pair of cylinders or at least two cylinders, e.g., a first cylinder member and a second cylinder member. The volumetric capacity of the inflatable member 104 may depend on the size of the cylinders. In some examples, the volume of fluid in each cylinder may vary from about 10 milliliters in smaller cylinders and to about 50 milliliters in larger sizes. In some examples, the first cylinder member may be larger than the second cylinder member. In other examples, the first cylinder member may have the same size as the second cylinder member.

In some embodiments, the inflatable member 104 is reinforced. In some embodiments, the reinforced inflatable member provides increased stiffness or rigidity. In some embodiments, the reinforced inflatable member provides improved reliability or longevity as the reinforced inflatable member may include less layers of material which can become degraded through friction and movement with respect to each other.

For example, in some embodiments, the inflatable member 104 includes a sidewall that defines the cavity that is configured to receive the fluid. In some embodiments, the sidewall of the inflatable member 104 includes portions or sections that have a larger size or width than other portions or sections of the inflatable member 104. The larger portions of the sidewall may provide strength or reinforcement to the inflatable member 104. In some embodiments, the sidewall includes projections, such as ridges or bumps. The projections may be included on (or extend from) either or both of an outer surface and an inner surface of the inflatable member 104. The projections may provide strength or reinforcement to the inflatable member 104.

In other embodiments, the inflatable member 104 includes a frame member or portion and a casing member or portion. The frame member may be coupled to the casing member and provide support or structure to the inflatable member 104. In some embodiments, the frame member is disposed on an outer surface of the casing member. In other embodiments, the frame member is disposed on an inner surface of the casing member. In yet other embodiments, the frame member is disposed within the casing member. In other words, the casing member surrounds or encases the frame member.

The reservoir 102 may include a container having an internal chamber configured to hold fluid that is used to inflate the inflatable member 104. The volumetric capacity of the reservoir 102 may vary depending on the size of the inflatable penile prosthesis 100. In some examples, the volumetric capacity of the reservoir 102 may be 40-50 cubic centimeters. In some examples, the reservoir 102 is constructed from the same material as the inflatable member 104. In other examples, the reservoir 102 is constructed from a different material than the inflatable member 104.

In some examples, the reservoir 102 may be pressurized. In some examples, the reservoir 102 is pressurized less than or equal to a pressurized threshold. In some examples, the reservoir 102 is pressurized to be equal to or less than diastolic pressure in order to ensure that the reservoir 102 is not over pressurized. In some examples, the pressurized threshold is 70 mm/Hg. In some examples, the pressurized threshold is greater than 70 mm/Hg. In other examples, the pressurized threshold is less than 70 mm/Hg. In some examples, the reservoir 102 includes a pressure regulating balloon. In other examples, the reservoir 102 is not pressurized (e.g., static). In some examples, reservoir 102 may include a single container configured to hold the fluid, which may or may not be pressurized. In some examples, the reservoir 102 includes a primary container (or primary chamber) and a secondary container (or secondary chamber), where the primary container/chamber may hold the fluid that is transferred to the inflatable member 104, and the secondary container/chamber may include gas or secondary fluid that is used to pressurize the fluid in the primary container/chamber.

The inflatable penile prosthesis 100 may include a first conduit connector 103 and a second conduit connector 105. Each of the first conduit connector 103 and the second conduit connector 105 may define a lumen configured to transfer the fluid to and from the pump assembly 101. The first conduit connector 103 may be coupled to the pump assembly 101 and the reservoir 102 such that fluid can be transferred between the pump assembly 101 and the reservoir 102 via the first conduit connector 103. For example, the first conduit connector 103 may define a first lumen configured to transfer fluid between the pump assembly 101 and the reservoir 102. The first conduit connector 103 may include a single or multiple tube members for transferring the fluid between the pump assembly 101 and the reservoir 102.

The second conduit connector 105 may be coupled to the pump assembly 101 and the inflatable member 104 such that fluid can be transferred between the pump assembly 101 and the inflatable member 104 via the second conduit connector 105. For example, the second conduit connector 105 may define a second lumen configured to transfer fluid between the pump assembly 101 and the inflatable member 104. The second conduit connector 105 may include a single or multiple tube members for transferring the fluid between the pump assembly 101 and the inflatable member 104. In some examples, the first conduit connector 103 and the second conduit connector 105 may include a silicone rubber material.

The pump assembly 101 may switch between an inflation mode in which the fluid in the reservoir 102 is transferred to the inflatable member 104 through the pump assembly 101 in a first direction (e.g., inflation direction) and a deflation mode in which the fluid in the inflatable member 104 is transferred back to the reservoir 102 through the pump assembly 101 in a second direction (e.g., deflation direction).

The pump assembly 101 may include a pump 106 and a valve body 107. The valve body 107 also includes a selection member 109. The selection member 109 may be used to select or change the mode in which the pump assembly is in. For example, the selection member 109 may be moved from a first position to a second position to place the device in its deflation mode. The selection member 109 may then be moved back to its first position to place the device in its inflation mode. In some embodiments, the selection member 109 is movable with respect to the valve body 107. For example, in some embodiments, the selection member 109 is slidably coupled or slideable with respect to the valve body 107.

The pump 106 may be squeezed or depressed by the user in order to facilitate the transfer of fluid from the reservoir 102 to the inflatable member 104. For example, in the inflation mode, while the user is operating the pump 106, the pump 106 may receive the fluid from the reservoir 102, and then output the fluid to the inflatable member 104. When the user switches to the deflation mode, at least some of the fluid can automatically be transferred back to the reservoir 102 (due to the difference in pressure from the inflatable member 104 to the reservoir 102). Then, the user may squeeze the inflatable member 104 to facilitate the further transfer of fluid through the pump 106 to the reservoir 102.

In some examples, the pump 106 may include a flexible member defining a cavity. In some examples, the pump 106 may define a pump shell having a flexible bulb and a valve body connector, where the valve body connector is designed to fit at least partially over the valve body 107. In some examples, the pump 106 may include a squeeze pump. In some examples, the pump 106 may include a portion that is round or substantially round. In some examples, the pump 106 may include ribbing or dimples to aid the user in gripping the pump 106. The pump 106 may use suction and pressure to move the fluid in and out of the cavity of the pump 106 in the inflation mode. For example, the user may depress or squeeze the pump 106 to expel the fluid out of the cavity, and, when the flexible member returns to its original shape, the resulting suction pushes the fluid into the cavity of the pump 106. In some examples, the pump 106 may have a bulb spring rate that is designed to refill the pump 106 in a selected time frame.

As discussed above, the selection member 109 may be used to select or change the mode in which the pump assembly is in. In some embodiments, the selection member 109 includes or defines at least one opening, hole, or lumen. The selection member 109 is configured to be moved from one position in which it allows fluid to flow through one or more of the channels and another position in which it allows fluid to flow though a different or a different set of channels. For example, in one embodiment, the selection member 109 may be placed in the inflate position and the user may then operate the pump 106 to inflate the inflatable member 104 (i.e., move the fluid from the reservoir 102 to the inflatable member 104). For example, the user may repeatedly depress or squeeze the pump 106 until the desired rigidity is achieved.

In some examples, if the reservoir 102 is at least partially pressurized, the fluid may automatically flow out of the reservoir 102 and into the inflatable member 104 without the user depressing or squeezing the pump 106 until the pressure is at least partially equalized between the reservoir 102 and the inflatable member 104.

Then, when the user wants to deflate the inflatable member 104, the user moves selection member 109 to its deflate position. The user may then operate the pump 106 to deflate the inflatable member 104 (i.e., move the fluid from the inflatable member 104 to the reservoir 102). The pump 106 may then return to its original form, which provides a suction force causing fluid to be drawn into the pump 106 from the inflation member 104. The fluid from the inflation member 104 fills the pump 106 (or at least partially fills the pump 106). This pump cycle is repeated until the inflatable member 104 is deflated.

In some examples, the fluid may automatically (upon movement of the selection member 109 to its deflate position) flow out of the inflatable member 104 and into the reservoir 102 without the user depressing or squeezing the pump 106 until the pressure is at least partially equalized between the reservoir 102 and the inflatable member 104.

In some examples, after the inflation member 104 has been deflated, the pump 106 may be squeezed to place the pump in a contracted position or configuration.

Figure 2:
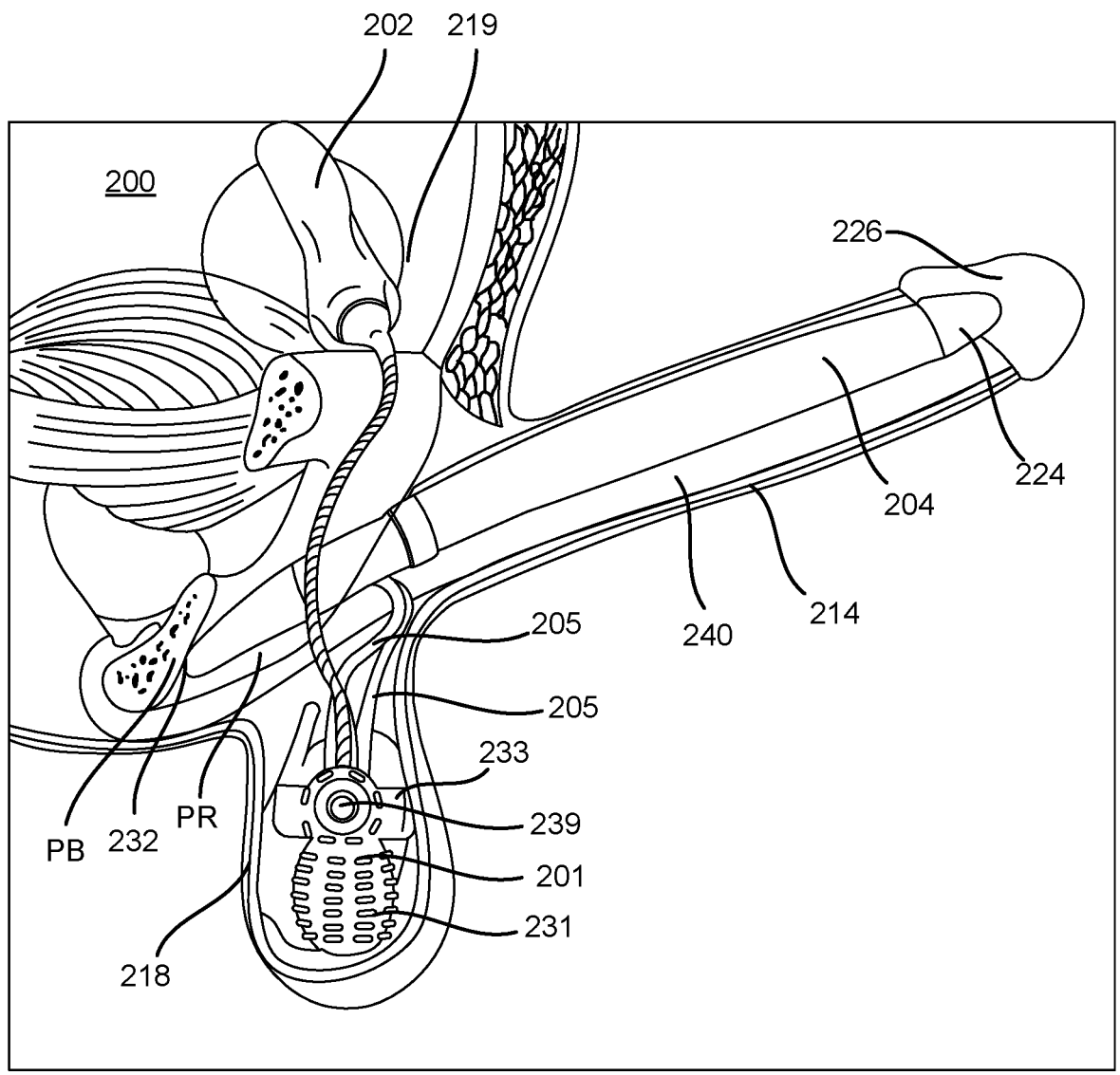
FIG. 2 illustrates an inflatable penile prosthesis implanted within a patient according to an embodiment.
Figure 3:
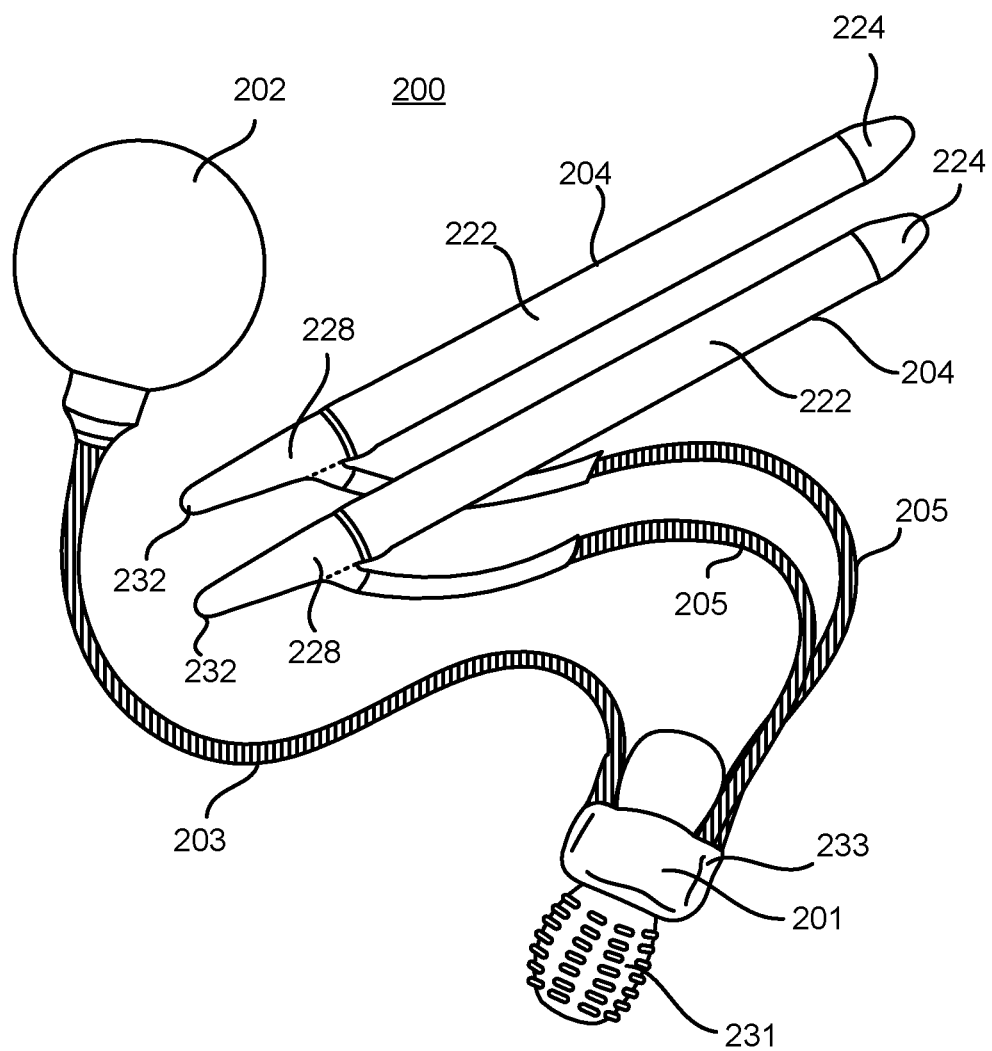
FIG. 3 is a perspective view of the inflatable penile prosthesis of FIG. 2.

FIG. 2 illustrates an inflatable penile prosthesis 200 implanted within a user according to an aspect. FIGS. 3-6 illustrate the inflatable penile prosthesis 200.

The inflatable penile prosthesis 200 may include a pair of cylinders 204, and the pair of cylinders 204 are implanted in a penis 214. For example, one of the cylinders 204 may be disposed on one side of the penis 214. The other cylinder 204 (not shown in FIG. 2) of the pair of cylinders may be disposed on the other side of the penis 214. The cylinder 204 may include a distal end portion 224, a cavity or inflation chamber 222, and a proximal end portion 228 having a rear tip 232.

The inflatable penile prosthesis 200 may include a pump assembly 201, which may be implanted into the patient's scrotum 218. A pair of conduit connectors 205 may attach the pump assembly 201 to the pair of inflatable members or cylinders 204 such that the pump assembly 201 is in fluid communication with the pair of inflatable members or cylinders 204. Also, the pump assembly 201 may be in fluid communication with a reservoir 202 via a conduit connector 203. The reservoir 202 may be implanted into the user's abdomen 219. The inflation chamber or portion 222 of the cylinder 204 may be disposed within the penis 214. The distal end portion 224 of the cylinder 204 may be at least partially disposed within the crown portion 226 of the penis 214. The proximal end portion 228 may be implanted into the patient's pubic region PR with the rear tip 232 proximate the pubic bone PB.

In order to implant the inflatable members or cylinders 204, the surgeon first prepares the patient. The surgeon often makes an incision in the penoscrotal region, e.g., where the base of the penis 214 meets with the top of the scrotum 218. From the penoscrotal incision, the surgeon may dilate the patient's corpus cavernosae 240 to prepare the patient to receive the pair of inflatable members or cylinders 204. The corpus cavernosum is one of two parallel columns of erectile tissue forming the dorsal part of the body of the penis 214, e.g., two slender columns that extend substantially the length of the penis 214. The surgeon will also dilate two regions of the pubic area (proximal corpora cavernosae) to prepare the patient to receive the proximal end portion 228. The surgeon may measure the length of the proximal and distal corpora cavernosae from the incision and the dilated region of the pubic area to determine an appropriate size of the inflatable members or cylinders 204 to implant.

After the patient is prepared, the inflatable penile prosthesis 200 is implanted into the patient. The distal tip of the distal end portion 224 of each cylinder 204 may be attached to a suture. The other end of the suture may be attached to a needle member (e.g., Keith needle). The needle member is inserted into the incision and into the dilated corpus cavernosum. The needle member is then forced through the crown of the penis 214. The surgeon tugs on the suture to pull the cylinder 204 into the corpus cavernosum. This is done for each cylinder of the pair of cylinders 204. Once the inflation chamber 222 is in place, the surgeon may remove the suture from the distal tip. The surgeon then inserts the proximal end portion 228. The surgeon inserts the rear end of the cylinder 204 into the incision and forces the proximal end portion 228 toward the pubic bone PB until each cylinder 204 is in place.

In the illustrated embodiment, each of the inflatable members or cylinders 204 is structurally and functionally similar. Accordingly, only one of the inflatable members or cylinders will be discussed in detail. The inflatable member 204 may be capable of expanding upon the injection of fluid into a cavity of the inflatable member 204. For instance, upon injection of the fluid into the inflatable member 204, the inflatable member 204 may increase its length and/or width, as well as increase its rigidity. The volumetric capacity of the inflatable member 204 may depend on the size of the cylinders. In some examples, the volume of fluid in each cylinder may vary from about 10 milliliters in smaller cylinders and to about 50 milliliters in larger sizes.

Figure 4:
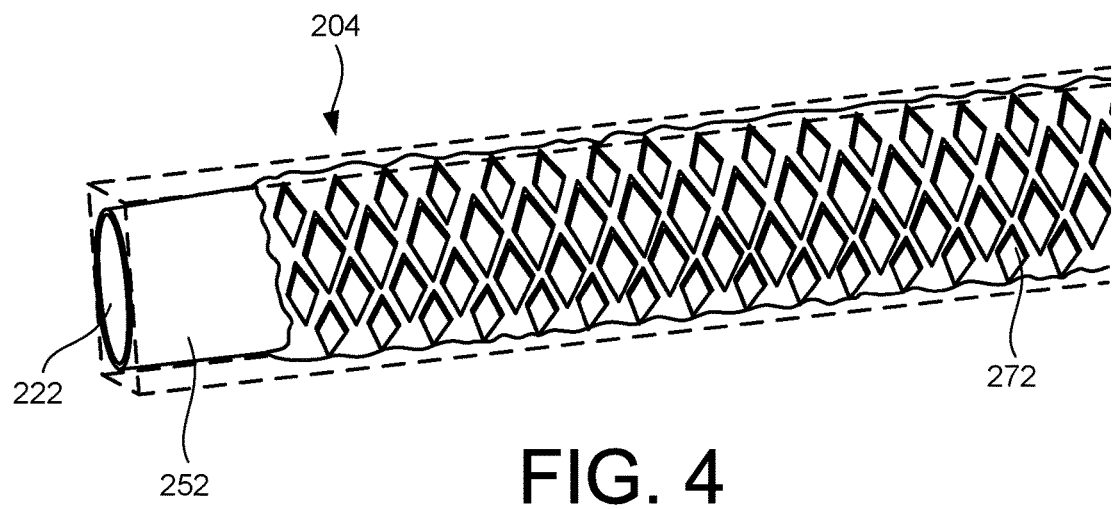
FIG. 4 is a perspective view of an inflatable member according to an embodiment.
Figure 5:
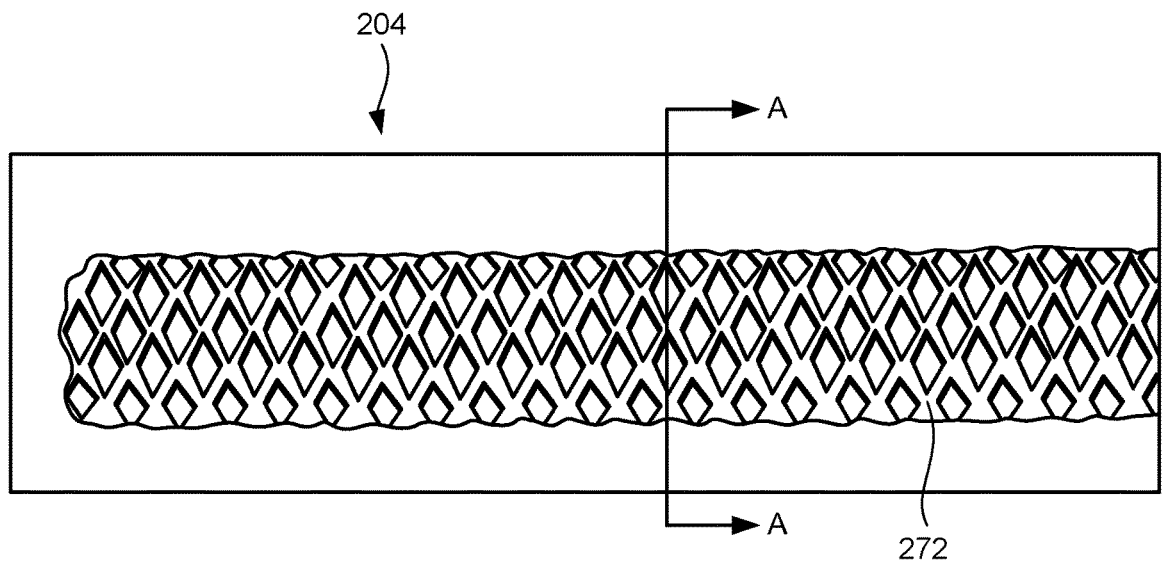
FIG. 5 is a side view of the inflatable member of FIG. 4.
Figure 6:
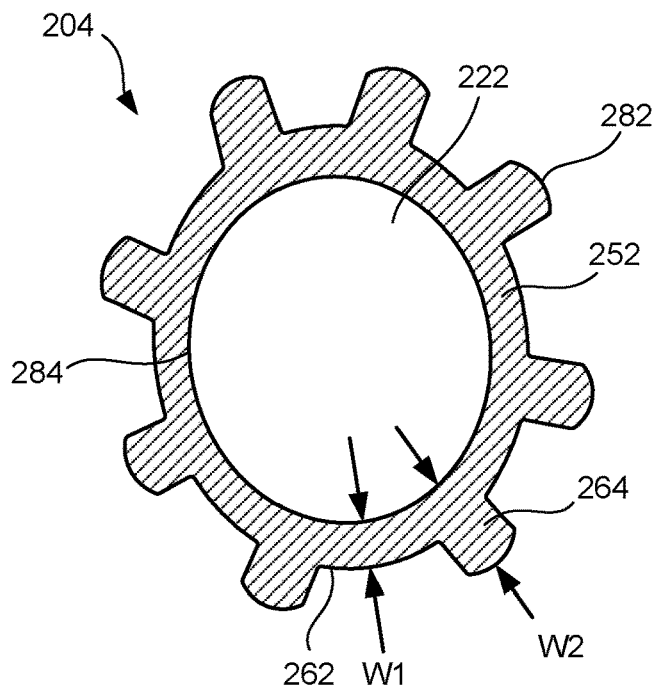
FIG. 6 is a cross-sectional view of the inflatable member of FIG. 4 taken along line A-A of FIG. 5.

As best illustrated in FIGS. 4-6, in the illustrated embodiment, the inflatable member 204 is reinforced. In some embodiments, the reinforcement provides increased stiffness or rigidity. In some embodiments, the reinforced inflatable member provides improved reliability or longevity as the reinforced inflatable member may include less layers of material which can become degraded through friction and movement with respect to each other. Additionally, the reinforcement may provide a specific inflation profile (a consistent inflation or an inflation that is varied) based on the location of the reinforcement along the inflatable member 204.

In the illustrated embodiment, the inflatable member 204 includes a sidewall 252 that defines the cavity or inflation chamber 222 that is configured to receive the fluid. Specifically, in the illustrated embodiment, the sidewall 252 of the inflatable member 204 includes portions or sections that have a larger size or width than other portions or sections of the inflatable member 204. As best illustrated in FIG. 6, portion 262 of the sidewall 252 has a width or size W1 and portion 264 of the sidewall 252 has a width or size W2. Width or size W2 is larger than width or size W1.

The larger portions of the sidewall 252 may provide strength or reinforcement to the inflatable member 204. For example, in some the illustrated embodiment, portion 264 of the sidewall 252 may have more strength than portion 262 of the sidewall 252. Additionally, portion 262 of the sidewall 252 may be configured to inflate, expand, or stretch more than portion 264 of the sidewall 252. In the illustrated embodiment, the sidewall 252 includes several sections that have larger widths or sizes and several sections that have smaller widths or sizes.

In the illustrated embodiment, the sidewall 252 includes an outer surface 282 and an inner surface 284. In the illustrated embodiment, the patterned portion 272 extends from the outer surface 282. Accordingly, the outer surface 282 includes a series of ridges and troughs. In other words, the outer surface 282 is not smooth or consistent. Rather, the outer surface is rough or not smooth. In the illustrated embodiment, the inner surface 284 is relatively smooth and does not include any ridges or troughs.

In some embodiments, the pattern 272 includes projections. In the illustrated embodiment, the projections are a series of lines, such as a series of intersection lines. In other embodiments, the projections are a series of bumps, domes, or dimples.

In some embodiments, the inflatable member 204 is single layer or single tube. In some embodiments, the inflatable member 204 is formed of or from a homogenous material. For example, in some embodiments, the inflatable member is formed of a biocompatible material. In some embodiments, the inflatable member is formed of a polymer or a polymeric material. In some embodiments, the inflatable member 204 includes an expansion rate or profile that simulates or matches that of a natural erection.

Figure 7:
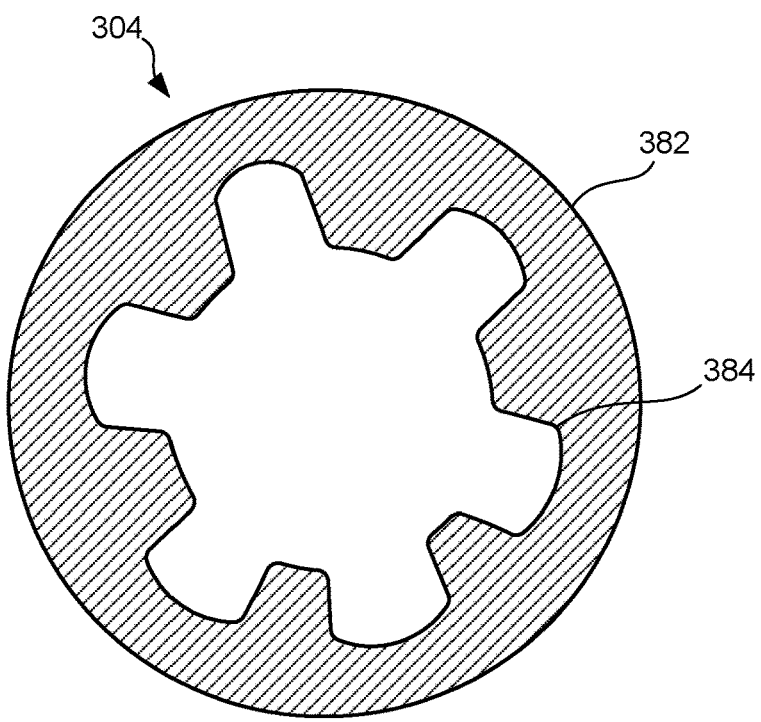
FIGS. 7-9 are cross-sectional views of inflatable members according to other embodiments.

In other embodiments, the inner surface includes a series or projections, ridges or troughs and the outer surface is relatively smooth. For example, as illustrated in FIG. 7, in one embodiment, the inflatable member 304 includes a sidewall 352. The outer surface 382 is relatively consistent or smooth and the inner surface 384 includes projections and is not smooth.

Figure 8:
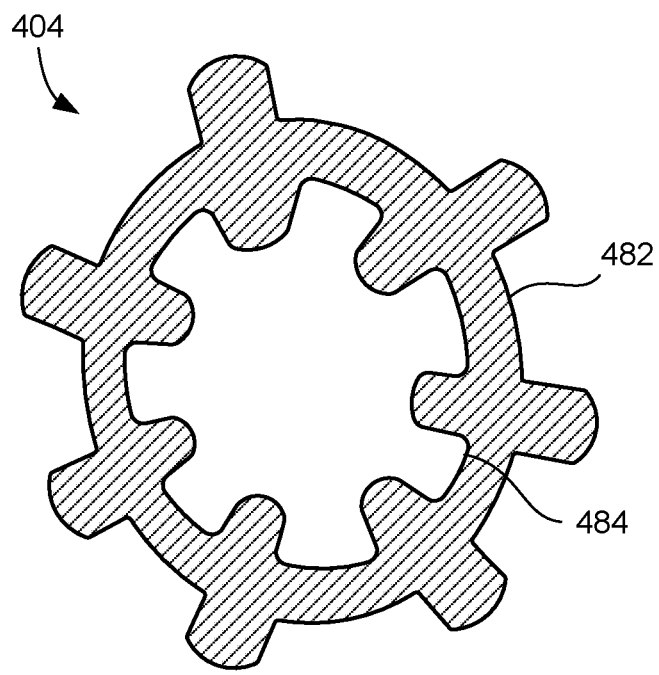
Figure 9:
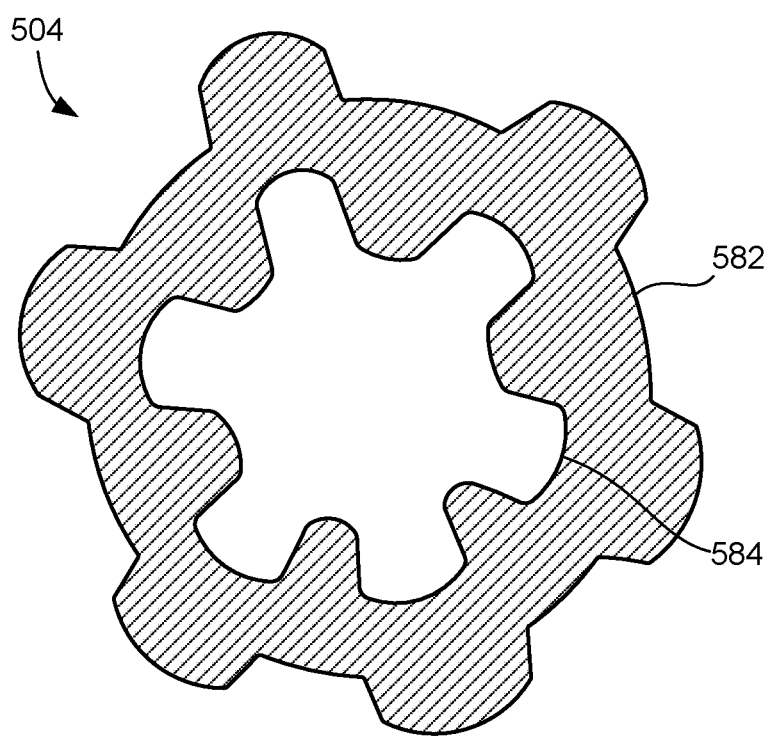

In yet other embodiments, both the inner surface and the outer surface include projections, ridges or troughs. For example, in FIG. 8, in one embodiment, the inflatable member 404 includes a sidewall 452. The outer surface 482 of the sidewall 452 includes projections and is not smooth and the inner surface 484 includes projections and is not smooth. As illustrated in FIG. 8, in one embodiment, the projections on the inner surface 484 are aligned with the projections of the outer surface 482. As illustrated in FIG. 9, in another embodiment of the inflatable member 504, the projections of the inner surface 584 are offset from the projections of the outer surface 582.

The pump assembly 201 may switch between an inflation mode in which the fluid in the reservoir 202 is transferred to the inflatable member 204 (or inflatable members) through the pump assembly 201 in a first direction (e.g., inflation direction) and a deflation mode in which the fluid in the inflatable member 204 (or inflatable members) is transferred back to the reservoir 202 through the pump assembly 201 in a second direction (e.g., deflation direction).

The pump assembly 201 includes a pump 231 and a valve body 233, and a selection member 239. The selection member may be used to select or change the mode in which the pump assembly 201 is in. For example, the selection member 239 may be moved from a first position to a second position to place the device in its deflation mode. The selection member 239 may then be moved back to its first position to place the device in its inflation mode. In some embodiments, the selection member 239 is movable with respect to the valve body 233. For example, the selection member 239 may be slidably coupled or slideable with respect to the valve body 233. In some embodiments, the selection member 239 includes stop members, such as shoulders or detents that engage members of the valve body 233 to lock or help retain the selection member 239 in one of its first and second positions.

The pump 231 may be squeezed or depressed by the user in order to facilitate the transfer of fluid from the reservoir 202 to the inflatable member 204. For example, in the inflation mode, while the user is operating the pump 231, the pump 231 may receive the fluid from the reservoir 202, and then output the fluid to the inflatable member 204. When the user switches to the deflation mode, at least some of the fluid can automatically be transferred back to the reservoir 202 (due to the difference in pressure from the inflatable member 204 to the reservoir 202). Then, the user may squeeze the inflatable member 204 to facilitate the further transfer of fluid through the pump 206 to the reservoir 202.

In the illustrated embodiment, the pump 231 includes a flexible member defining a cavity. In some examples, the pump may include a squeeze pump.

In some examples, if the reservoir 202 is at least partially pressurized, the fluid may automatically flow out of the reservoir 202 and into the inflatable member 204 without the user depressing or squeezing the pump 231 until the pressure is at least partially equalized between the reservoir 202 and the inflatable member 204.

Then, when the user wants to deflate the inflatable members 204, the user moves selection member 239 to its deflate position. The user may then operate the pump 231 to deflate the inflatable members 204 (i.e., move the fluid from the inflatable members 204 to the reservoir 202). For example, the user may repeatedly depress or squeeze the pump 231 until the deflation is completed. The pump 231 may then return to its original form, which provides a suction force causing fluid to be drawn into the pump 231 from the inflation members 204. The fluid from the inflation members 204 fills the pump 231 (or at least partially fills the pump 231). This pump cycle is repeated until the inflatable members 204 are deflated.

In some examples, the fluid may automatically (upon movement of the selection member 239 to its deflate position) flow out of the inflatable member 204 and into the reservoir 202 without the user depressing or squeezing the pump 231 until the pressure is at least partially equalized between the reservoir 202 and the inflatable member 204.

In some examples, after the inflation member 204 has been deflated, the pump 206 may be squeezed to place the pump in a contracted position or configuration.

Figure 10:
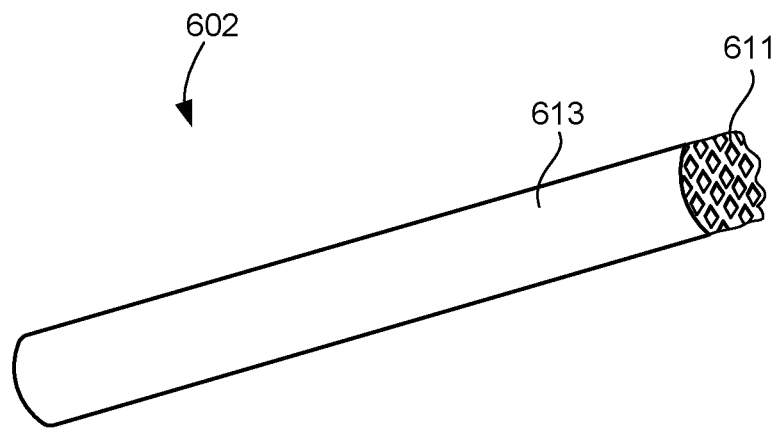
FIG. 10 is a perspective view of an inflatable member according to an embodiment.
Figure 11:
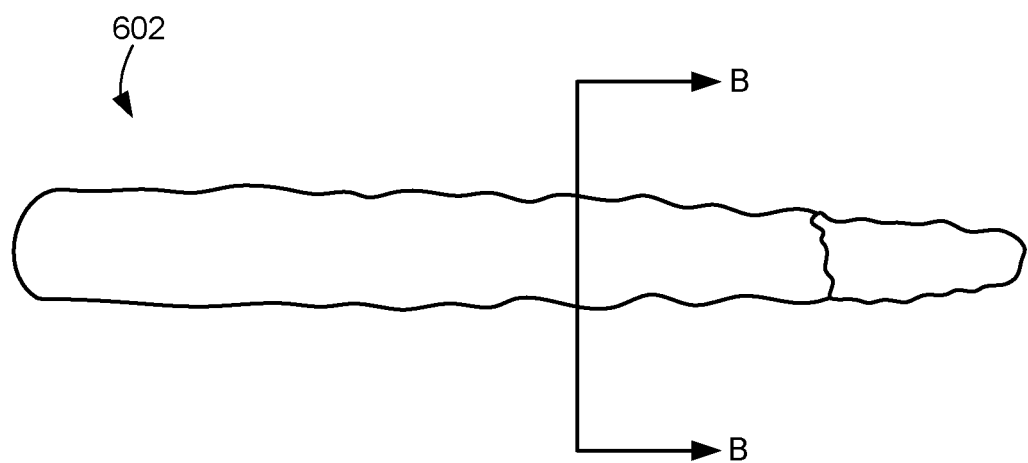
FIG. 11 is a side view of the inflatable member of FIG. 10.
Figure 12:
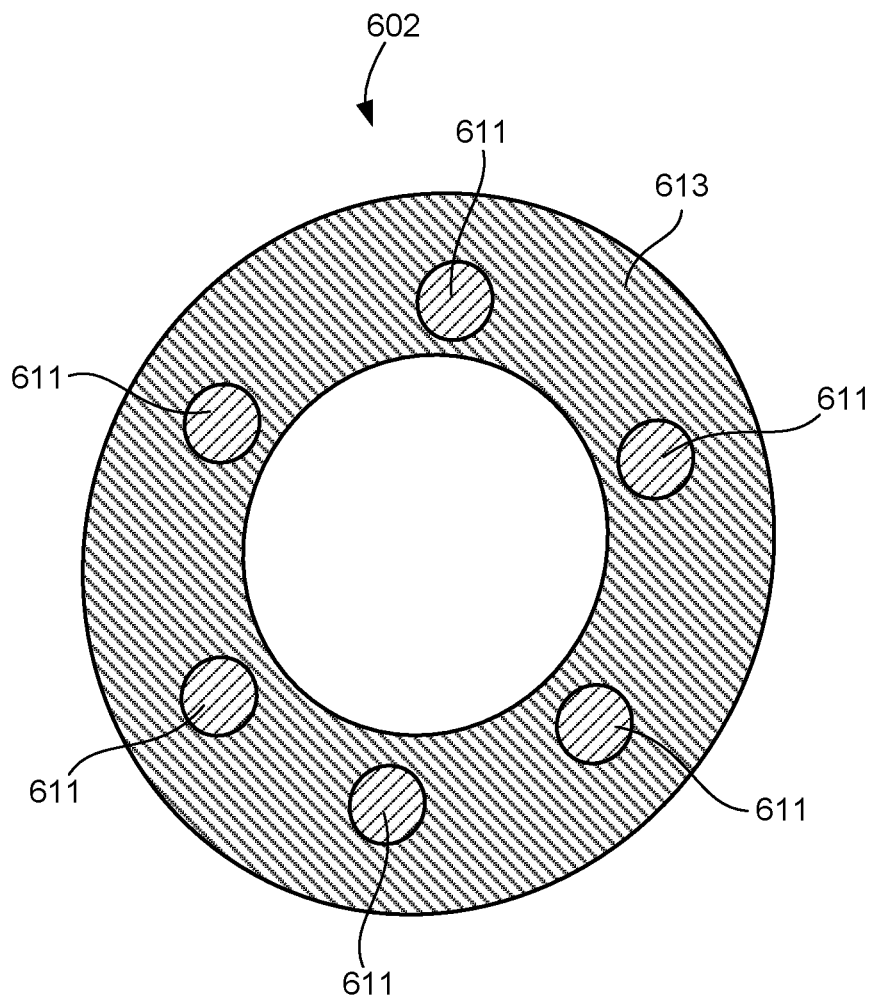
FIG. 12 is a cross-sectional view of the inflatable member of FIG. 10 taken along line B-B of FIG. 11.

FIGS. 10-12 illustrate an inflatable member 602 according to another embodiment. FIG. 10 illustrates the inflatable member 602 in a partial break-away view. In the illustrated embodiment, the inflatable member 602 includes a frame portion 611 and a casing portion 613.

The frame portion or member 611 is configured to provide strength and rigidity to the inflatable member 602. In some embodiments, the frame portion or member 611 is formed of a metal material. For example, in some embodiments, the frame portion or member 611 is formed of nitinol. In other embodiments, the frame portion or member 611 is formed of a polymer, such as an elastomeric polymer or a non-elastomeric polymer. In some embodiment, the frame portion or member 611 is configured to stretch or expand when the inflation member 602 is inflated. In some embodiments, the frame portion or member 611 is formed of a shape memory material. In some embodiments, the frame portion or member includes a plurality of member or portions that are interwoven or otherwise combined to form the frame portion or member.

The casing portion 613 is coupled to the frame portion or member 611. The casing portion 613 may be formed of a polymer material. In some embodiments, the casing portion 613 is formed of a elastomeric polymer. As best illustrated in 12, in the illustrated embodiment, the casing portion 613 surrounds the frame portion 611. In other words, the frame portion 611 is disposed within the casing portion 613. In other embodiments, the frame portion 611 may be disposed on or proximate an outer surface or an inner surface of the casing portion 613.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An inflatable penile prosthesis, comprising:
   an inflatable member, the inflatable member including a sidewall having an inner surface defining a lumen and an outer surface opposite the inner surface, the outer surface including a plurality of projections to reinforce the inflatable member and the inner surface including a plurality of projections to reinforce the inflatable member;
   a reservoir configured to hold fluid; and
   a pump assembly configured to facilitate a transfer of the fluid from the reservoir to the inflatable member when the prosthesis is in an inflation mode, and facilitate a transfer of the fluid from the inflatable member to the reservoir when the prosthesis is in a deflation mode.

2. The inflatable penile prosthesis of claim 1, wherein the sidewall of the inflatable member includes a first portion and a second portion, the first portion of the sidewall having a first thickness, the second portion of the sidewall having a second thickness, the first thickness being greater than the second thickness.

3. The inflatable penile prosthesis of claim 1, wherein the inflatable member is configured to stretch.

4. The inflatable penile prosthesis of claim 1, wherein the inflatable member is formed of an elastomeric polymer.

5. The inflatable penile prosthesis of claim 1, wherein the inflatable member is formed of a homogenous material.

6. The inflatable penile prosthesis of claim 1, wherein the inflatable member includes a frame portion to reinforce the inflatable member and a casing portion.

7. The inflatable penile prosthesis of claim 1, wherein the inflatable member includes a frame portion to reinforce the inflatable member and a casing portion, the casing portion surrounding the frame portion.

8. The inflatable penile prosthesis of claim 1, wherein the inflatable member includes a frame portion to reinforce the inflatable member and a casing portion, the frame portion includes a plurality of woven filaments.

9. A penile implant, comprising:
an inflatable member, the inflatable member having a sidewall having an inner surface defining a lumen and an outer surface opposite the inner surface, the outer surface including a plurality of projections to reinforce the inflatable member and the inner surface including a plurality of projections to reinforce the inflatable member;
a reservoir configured to the fluid; and
a pump assembly configured to facilitate a transfer of the fluid from the reservoir to the inflatable member.

10. The implant of claim 9, wherein the inflatable member is formed of a homogenous material.

11. The inflatable penile prosthesis of claim 1, wherein the plurality of projections of the outer surface are aligned with the plurality of projections of the inner surface.

12. The inflatable penile prosthesis of claim 1, wherein the plurality of projections of the outer surface are offset from the plurality of projections of the inner surface.

* * * * *